(12) United States Patent
Fäh et al.

(10) Patent No.: US 10,149,743 B2
(45) Date of Patent: Dec. 11, 2018

(54) INSTRUMENT FOR HANDLING A DENTAL PART

(71) Applicant: Cendres+Métaux SA, Biel/Bienne (CH)

(72) Inventors: Mathias Fäh, Solothurn (CH); Mathias Strazza, Meinisberg (CH); Matthias Walther, Münchenstein (CH)

(73) Assignee: CENDRES+METAUX SA (CH)

( * ) Notice: Subject to any disclaimer, the term of this patent is extended or adjusted under 35 U.S.C. 154(b) by 231 days.

(21) Appl. No.: 14/858,090

(22) Filed: Sep. 18, 2015

(65) Prior Publication Data
US 2016/0081774 A1 Mar. 24, 2016

(30) Foreign Application Priority Data

Sep. 19, 2014 (CH) .................................... 01412/14
Sep. 19, 2014 (CH) .................................... 01413/14

(51) Int. Cl.
*A61C 8/00* (2006.01)
(52) U.S. Cl.
CPC .......... *A61C 8/0089* (2013.01); *A61C 8/0087* (2013.01)
(58) Field of Classification Search
CPC ....... A61C 8/0027; A61C 8/0048; A61C 8/00; A61C 8/0028; A61C 8/0053
USPC ....................................................... 433/141
See application file for complete search history.

(56) References Cited

U.S. PATENT DOCUMENTS

| | | | | |
|---|---|---|---|---|
| 5,951,287 A * | 9/1999 | Hawkinson | ............ | A61C 8/005 433/141 |
| 5,964,591 A * | 10/1999 | Beaty | .................. | A61C 8/0001 433/141 |
| 6,159,008 A * | 12/2000 | Kumar | ................. | A61C 8/0087 433/141 |
| 6,203,323 B1 * | 3/2001 | Beaty | .................. | A61C 8/0001 433/141 |
| 6,261,097 B1 * | 7/2001 | Schmutz | .............. | A61C 8/0087 433/173 |
| 6,312,260 B1 | 11/2001 | Kumar et al. | | |
| 2001/0019816 A1 | 9/2001 | Kumar | | |
| 2004/0175673 A1 * | 9/2004 | Zickman | ................ | A61C 8/005 433/173 |

(Continued)

FOREIGN PATENT DOCUMENTS

DE 20 2007 004638 U1 6/2004
EP 0 986 341 B1 11/2004

(Continued)

OTHER PUBLICATIONS

European Search Report dated Dec. 19, 2014 issued in corresponding Swiss patent application No. 01412/14.

*Primary Examiner* — Nicholas Lucchesi
(74) *Attorney, Agent, or Firm* — Ostrolenk Faber LLP

(57) ABSTRACT

The instrument (10) for handling a dental part (50), for example, a male part, extends in a longitudinal axis (11) between a handling end (10*c*) and a connecting end (10*a*) for connection to the dental part (50). The connecting end (10*a*) has a receiving opening for receiving the head (51) of the dental part (50), which is laterally open, so that the connecting end (10*a*) and the dental part (50) can be connected by displacing them relative to one another transversely to the longitudinal axis (11). The male part (50) includes a head end having at least one protrusion, (53*a*) with which a stop (17*b*) that is formed on the instrument (10) can be contacted for transferring a torque generated on the instrument.

11 Claims, 6 Drawing Sheets

(56) References Cited

U.S. PATENT DOCUMENTS

| | | | |
|---|---|---|---|
| 2005/0170311 A1* | 8/2005 | Tardieu | A61C 8/0089 433/76 |
| 2006/0172255 A1* | 8/2006 | Hochman | A61C 8/0089 433/144 |
| 2006/0269890 A1 | 11/2006 | Mundwiler et al. | |
| 2010/0003634 A1* | 1/2010 | Cousley | A61C 8/00 433/72 |
| 2010/0248180 A1* | 9/2010 | Bondar | A61C 8/0001 433/141 |
| 2011/0014586 A1* | 1/2011 | Jorneus | A61C 8/0075 433/173 |
| 2011/0143315 A1 | 6/2011 | Guenter et al. | |
| 2013/0065197 A1 | 3/2013 | Mamraev | |
| 2015/0182309 A1* | 7/2015 | Soler | A61C 8/0001 433/174 |
| 2015/0250565 A1* | 9/2015 | Gustafsson | A61C 8/0089 433/127 |

FOREIGN PATENT DOCUMENTS

| | | |
|---|---|---|
| EP | 2 281 527 A1 | 2/2011 |
| EP | 2 567 672 A2 | 3/2013 |
| KR | 2013 0025481 | 3/2013 |
| KR | 101 360 952 B1 | 2/2014 |
| WO | WO 01/50978 A1 | 7/2001 |

\* cited by examiner

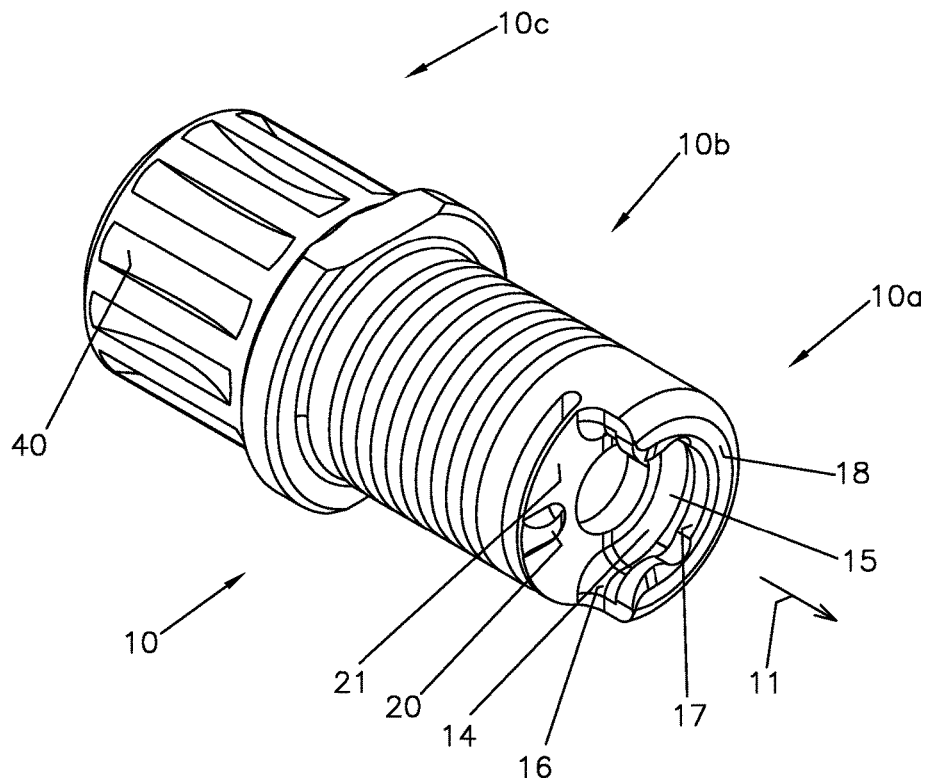
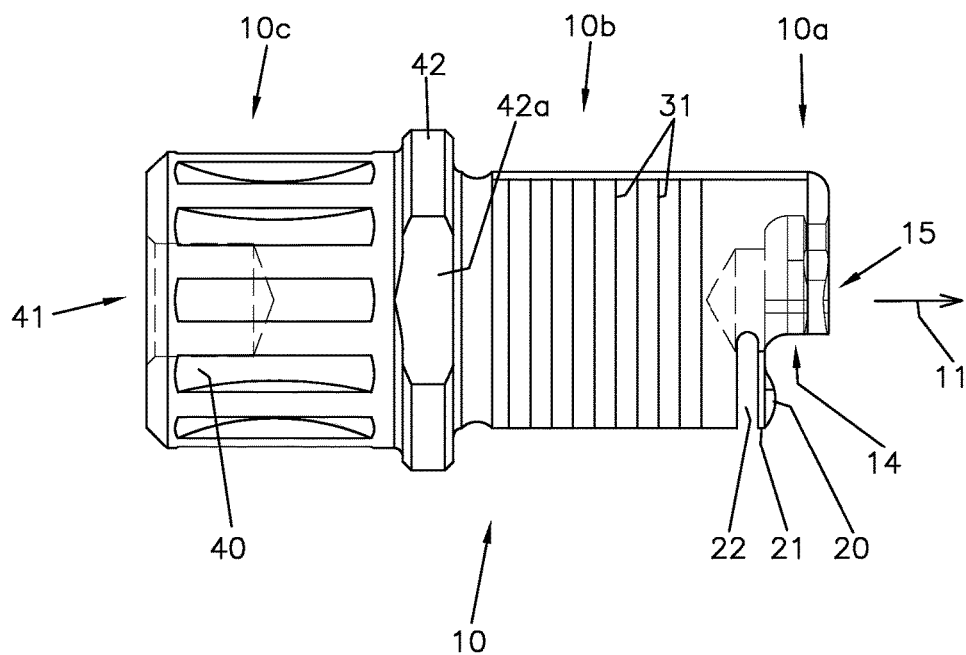

INSTRUMENT FOR HANDLING A DENTAL PART

BACKGROUND OF THE INVENTION

The invention relates to an instrument for handling a dental part, e.g. a male part.

Such instruments are designed, for example, in the form of screwdrivers such as those known from EP 0 986 341 A1, EP 2 281 527 A1 and EP 2 567 672 A2. These instruments have a connecting end designed to be open at the front to receive the head of the dental part. The instrument and the dental part are thus brought into connection with one another by displacing them relative to one another in the direction of the longitudinal axis. However, the space conditions may be limited, for example, if the dental part is to be introduced into a patient's mouth so that placement of the instrument on the dental part is made difficult.

SUMMARY OF THE INVENTION

The object of the present invention is to provide an instrument which facilitates the handling of a dental part, and to provide a male part to be connected to the instrument to facilitate the handling of the dental part.

This object is achieved by an instrument comprising a connecting end, which comprises a receiving opening that is laterally open, so that the connecting end and the dental part are apt to be connected by displacing them relative to one another transversely to the longitudinal axis of the instrument, and a male part that is to be connected to the instrument. This design facilitates handling because a dental part fastened in the mouth, for example, can be released in that the instrument is placed on the dental part by displacing it laterally.

Preferably, the connecting end of the instrument comprises at least one holding element for holding the head of the dental part received in the receiving opening to counteract separation of the connecting end and the head. This reduces the risk that the dental part might unintentionally fall away from the instrument during handling and under some circumstances might enter the patient's esophagus or, even worse, the patient's trachea ("aspiration-proof handling").

Preferably, the connecting end comprises at least one stop that is apt to be contacted with a protrusion formed on the dental part, in particular a male part, in that the instrument and the dental part are rotated about the axis of rotation relative to one another after being joined. This design has the particular advantage that the instrument need not to be aligned accurately with respect to the dental part when used as a screwdriver in order to be able to position it or remove it, since it is possible to join or separate the instrument and the dental part even if the instrument is rotated by an angle about the longitudinal axis with respect to the dental part.

BRIEF DESCRIPTION OF THE DRAWINGS

Additional specific design features and their advantages are apparent from the following description and drawings of an exemplary embodiment, in which FIG. 1 shows a perspective view of an instrument according to the invention, FIG. 2 shows the instrument from FIG. 1 in a side view.

FIGS. 1-7 show an instrument 10, which serves to handle a dental part 50 as shown in FIGS. 8-10, for example. The instrument 10 is shown here for use as a screwdriver for rotating the dental part 50 and therefore is referred to as such in the following.

DETAILED DESCRIPTION OF THE PREFERRED EMBODIMENTS

Figure 3:
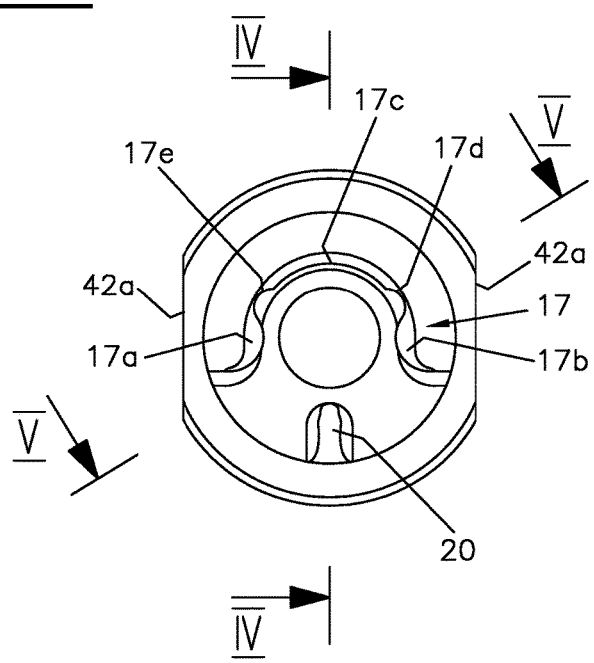
FIG. 3 shows the instrument from FIG. 1 in a front view.
Figure 4:
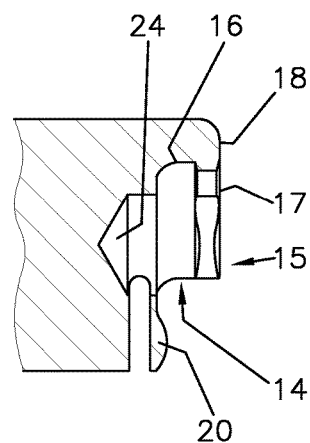
FIG. 4 shows the instrument from FIG. 1 in a sectional view according to line IV-IV in FIG. 3.

The screwdriver 10 extends in the longitudinal axis 11, which corresponds here to the axis of rotation, about which the dental part 50 is to be rotated. It comprises a connecting end 10a, a handling end 10c and a middle part 10b connecting these two ends. The connecting end 10a serves to receive the dental part, so that it can be handled. For example, the dental part can be rotated by rotating the connecting end 10a about the axis of rotation 11. The connecting end 10a has a laterally open receiving opening 14 into which the head of the dental part can be inserted by moving it into the receiving opening 14 transversely to the axis of rotation 11. At the front end, the connecting end 10a comprises a through-opening 15, which joins the receiving opening 14 and through which the dental part protrudes when its head is received in the receiving opening 14.

The wall of the connecting end 10a is shaped, so that it forms a groove 16 on which a shoulder 17 is adjacent, its outside being part of the front end face 18 of the connecting end 10a. The groove 16 and the shoulder 17 do not extend around the full circumference but instead cover only an angle range of less than 360 degrees, preferably less than 270 degrees (cf. FIG. 3).

Figure 13:
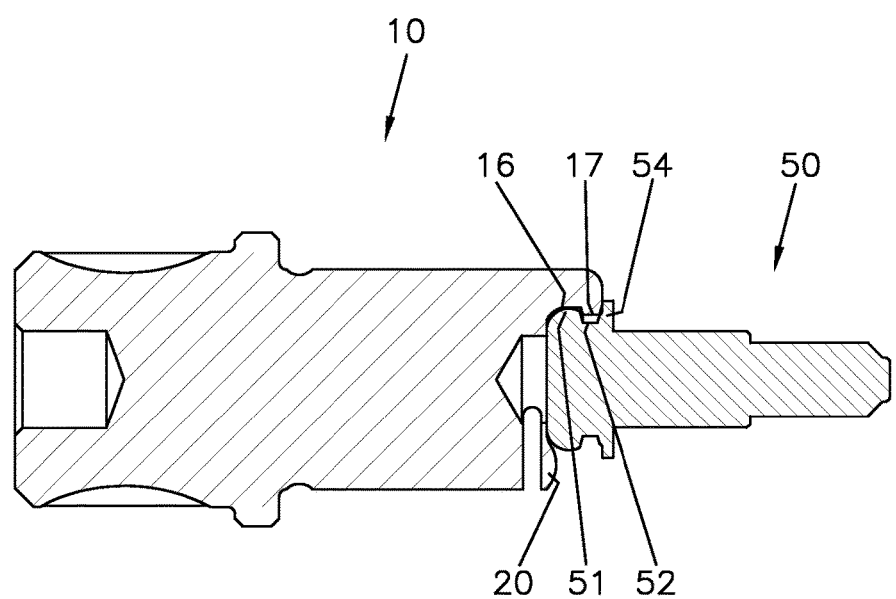
FIG. 13 shows the arrangement according to FIG. 11 in a longitudinal section.

The groove 16 is designed to be essentially complementary to the corresponding part of the dental part 50, so that this part contacts the wall of the groove 16 when its head is accommodated in the connecting end 10a (cf. FIG. 13).

Figure 6:
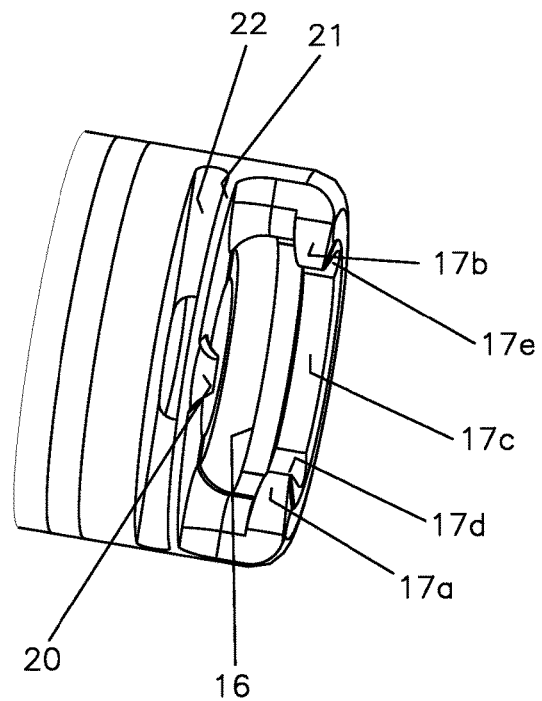
FIG. 6 shows a detailed view of the connecting end of the instrument from FIG. 1.

The shoulder 17 is designed with a thickened area on each end, which protrudes more toward the inside there, i.e., toward the axis of rotation 11, than in its middle part 17c (cf. the thickened ends 17a, 17b in FIGS. 3 and 6). As explained further below, the respective end 17a, 17b forms a stop for the dental part 50 to be able to transfer the torque of the screwdriver 10. Here, the shoulder 17 has a location 17d, 17e with a reduced wall thickness between the middle part 17c of the shoulder 17 and the respective end 17a, 17b in that the shoulder 17 there runs radially outward, i.e., away from the axis of rotation 11. The locations 17d, 17e may also be omitted.

Figure 5:
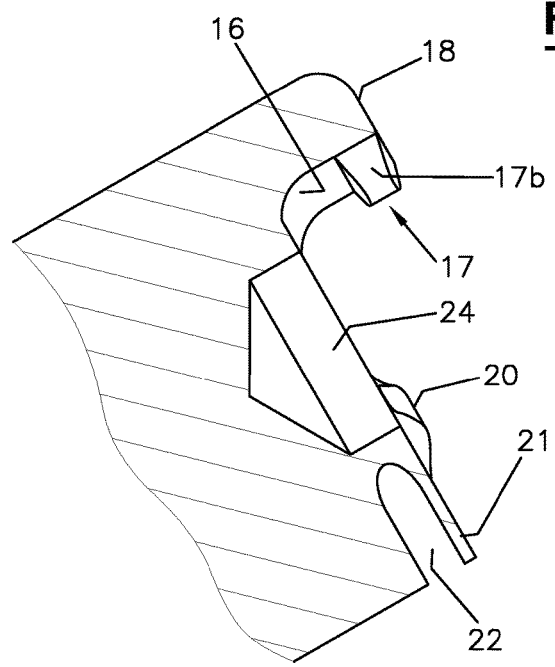
FIG. 5 shows the instrument from FIG. 1 in a sectional view according to line V-V in FIG. 3.

The connecting end 10a also has one or more holding means which prevent the dental part from falling out when it is accommodated in the receiving opening 14. The holding means here comprise a nose 20, which is situated on the level of the groove 16. When seen in the direction of the axis of rotation 11, the nose 20 is in the middle region between the two ends of the groove 16 (cf. FIG. 3). The nose 20 is supported, so that it can move axially (i.e., in the direction of the axis of rotation 11). For this purpose, the nose 20 is arranged on a lamellar element 21, which is held at one end, so that it can move elastically in the axial direction. The lamellar element 21 is formed here in the form of a section of a perforated disk, which is connected at the end to the wall in which the groove 16 is formed. The lamellar element 21 is arranged at a distance from the middle part 10b, so that movement in the axial direction is possible (cf. the empty space 22 in FIG. 2, 5 or 6).

In the extension of the through-opening 15, the middle part 10b of the screwdriver 10 has a blind hole 24. This is the result of the process engineering in the manufacture of the lamellar element 21, for example.

Figure 7:
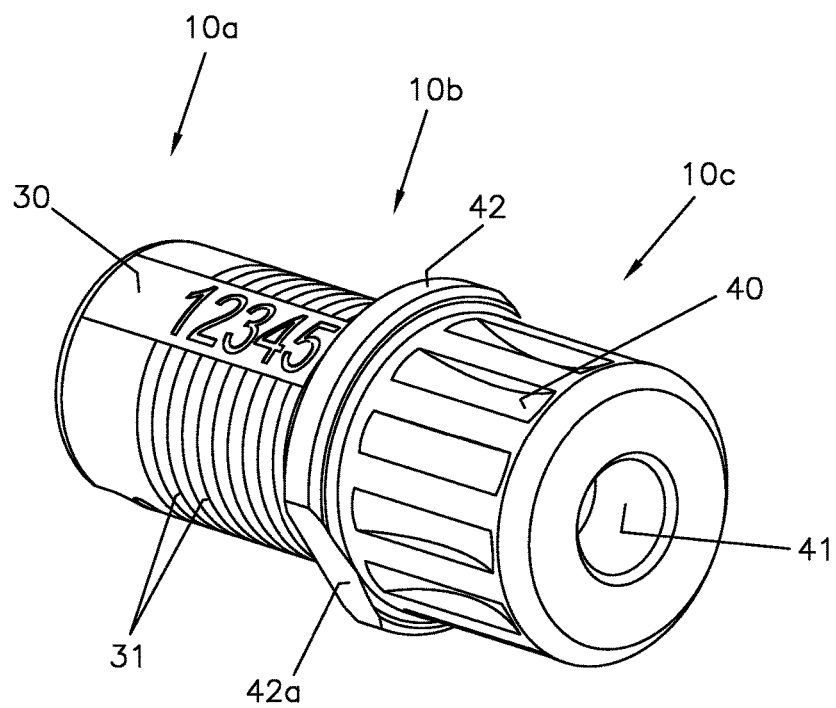
FIG. 7 shows another perspective view of the instrument from FIG. 1.

The middle part 10b is designed here as a body, which is essentially cylindrical. Marks are provided on the outside to serve as a scale, shown here in the form of equidistant lines. As FIG. 7 shows, a dimension scale 30, which is provided with numerals 1 to 5 here, is also provided on the outside of the middle part 10b. This scale of dimensions may of course also be designed differently or omitted entirely. If present, the scale of dimensions 30 and the marks 31 form a measure that makes it possible to determine the height above a certain level. For example, this makes it easier for the dentist to select the size of a suitable abutment by placing the screwdriver 10 on the implant and/or the abutment on the implant and reading from the marks 31 to ascertain the level at which an abutment of a certain size comes to lie.

The handling end 10c of the screwdriver 10 is designed for the respective purpose. The handling end 10c here is designed so that it can be connected to another tool to rotate the screwdriver 10 together with a dental part accommodated therein. The handling end 10c has a head with external profiling 40, which is designed complementary to the connecting head of a torque wrench ("ratchet") for forming a rotationally fixed connection. Such a tool is used to be able to exert a defined tightening torque on the dental part to be affixed in the mouth.

As shown in FIG. 7 the handling end 10c has a blind hole 41 on the front end, which serves as a counterholder during tightening and/or loosening.

The middle part 10b is connected to the handling end 10c via a collar 42 that has flattened areas 42a to prevent rolling when handling.

The head of the handling end 10c may also have a different design and is adapted according to the design of the tool to be connected to it. For example, if a connection to an angle piece used by the dentist is intended, the head of the handling end 10c can be designed as an ISO connection.

If necessary, the user can also handle the screwdriver 10 directly with his fingers by using the handling end 10c as a grip.

The screwdriver 10 can be manufactured from conventional materials, such as plastic and/or metal, as an individual part or in multiple parts.

Figure 8:
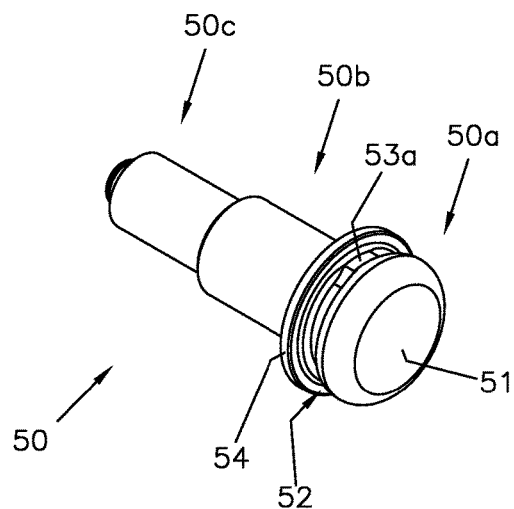
FIG. 8 shows a perspective view of a dental part that can be handled with the instrument according to FIG. 1.
Figure 9:
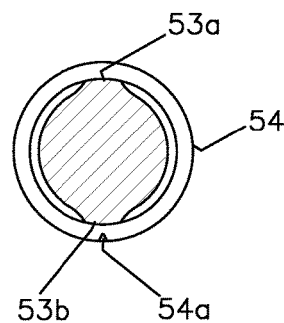
FIG. 9 shows a sectional top view of the dental part from FIG. 8.
Figure 10:
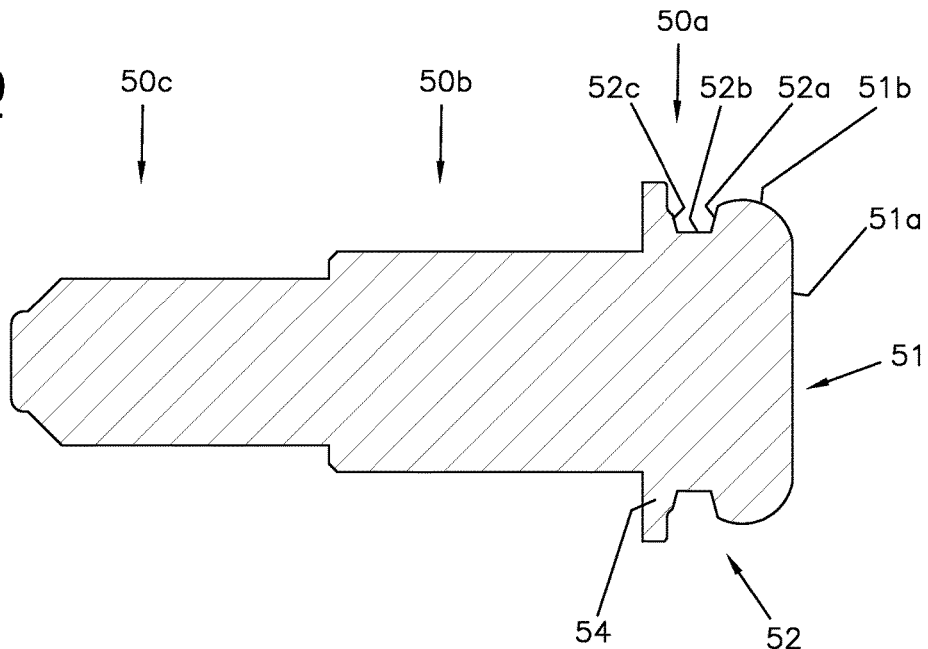
FIG. 10 shows a sectional side view of the dental part from FIG. 8.

One example of a dental part 50 that can be handled with the screwdriver 10 is shown in FIGS. 8-10. In the present exemplary embodiment, the dental part 50 serves as a male part that can be connected to a corresponding counterpart ("female part") to be able to attach a dental prosthesis, e.g. a denture, detachably in the mouth. The male part is designed here as an abutment having a connecting end 50a that is connected to a fastening end 50c by means of a middle male part 50b. The middle male part 50b and the fastening end 50c are designed so that the abutment 50 can be fastened to an implant. To this end, the fastening end 50c has a thread, for example, which can be screwed into a complementary thread on the implant.

Depending on the application, the parts 50b and 50c can also be designed so that the male part 50 can be attached to a root pin, a root anchor, a bar, or directly into a bone or a dental root. To this end, the male part may have a threaded end.

As shown in FIG. 10 in particular, the connecting end 50a of the male part 50 has a head 51 on the end face with a contour, which has a convex and/or planar shape. In the present example, the contour has a planar end face 51a, which is adjacent laterally to a circumferential round surface 51b, which has a circular cross section here. The head 51 is preferably free of edges that can disturb a user when used in the mouth and/or is free of concave surfaces, in particular recesses, which make cleaning difficult, among other things. The surface 51b is adjacent to a groove 52 which has two side surfaces 52a and 52c, between which a bottom surface 52b is arranged. The side surfaces 52a and 52c are directed toward one another, as seen in cross section, so that the groove 52 tapers in the direction towards the bottom surface 52b. Thereby, connection with the screwdriver 10 is facilitated, among others.

As shown in FIGS. 8 and 9 in particular, the connecting end 50a has protrusions 53a, 53b, which are designed here in the form of thickened areas arranged at the level of the groove 52. As can be seen from FIG. 9, a protrusion 53a, 53b extends over an angular range around the longitudinal axis of the male part 50, which is less than 180 degrees, preferably less than 90 degrees and most preferably less than 45 degrees. As explained further below, the protrusions 53a, 53b serve to transfer the torque of the screwdriver 10. Two protrusions 53a, 53b are provided here. Depending on the design, a single protrusion 53a or 53b may also be sufficient.

A circumferential collar 54, which is designed disc-shaped in the present example, is adjacent to the groove 52. As shown in FIG. 10, it protrudes laterally and has a larger diameter here than the head 51. The collar 54 is adjacent to the middle male part 50b and may have a mark which serves as an aid to determine the angular alignment of the male part 50. The mark is formed as a notch 54a here which is situated in the region of the thickened area 53b (cf. FIG. 9). The mark may also be provided somewhere else, e.g., on the head 51.

Figure 11:
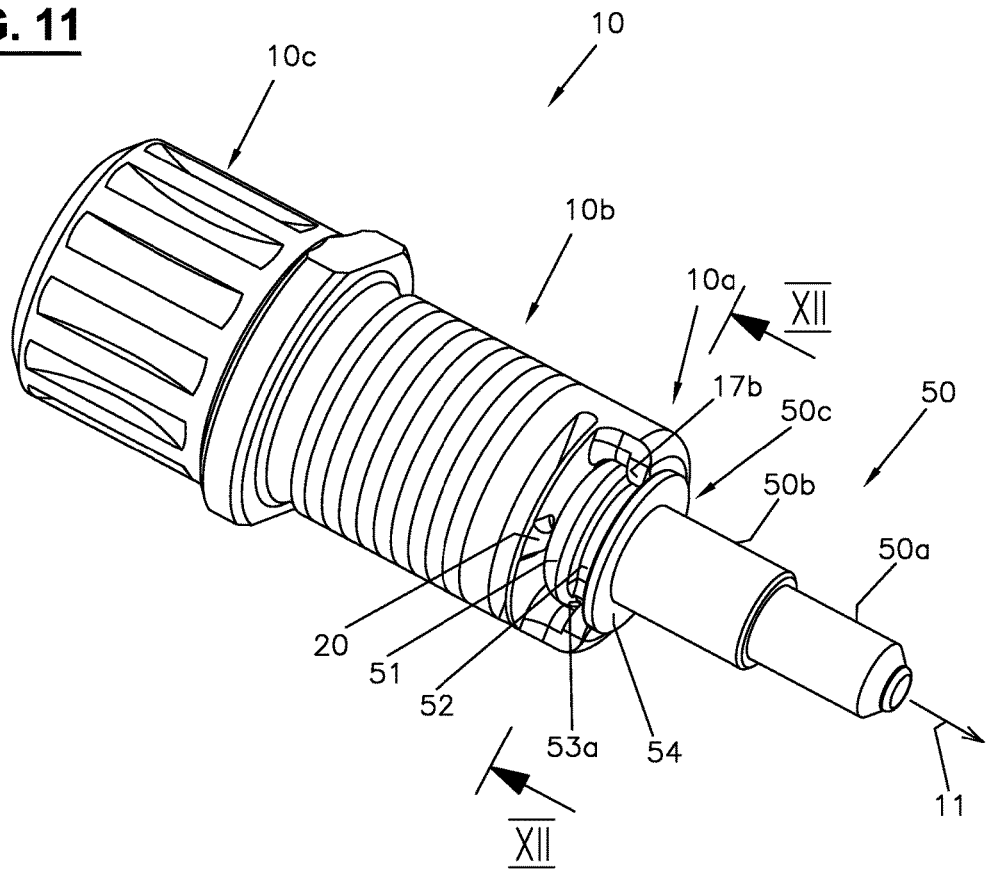
FIG. 11 shows a perspective view of the instrument from FIG. 1 and the dental part from FIG. 8 after joining them together.

A dental part, for example, the male part 50 from FIGS. 8-10 can be handled as follows by means of the screwdriver 10 (cf. FIGS. 11-13):

The connecting end 50a of the male part 50 is inserted into the laterally open receiving opening 14 of the screwdriver 10 by moving the male part 50 relative to the screwdriver 10 transversely to the axis of rotation 11. On insertion, the nose 20 on the screwdriver 10 is pushed out of the resting position and returns to the resting position as soon as the head 51 of the male part 50 comes to lie in the groove 16 of the screwdriver 10. The male part 50 is laterally held by the nose 20, which prevents it from falling out unintentionally. The shoulder 17 of the screwdriver 10 engages in the groove 52 of the male part 50. The collar 54, which is in contact with the end face 18 of the screwdriver 10 here, as well as the middle male part 50b and the connecting end 50a protrude through the through-opening 15 (cf. FIG. 1).

After insertion, the thickened ends 17a, 17b on the screwdriver 10 and the protrusions 53a, 53b on the male part 50 are usually arranged a distance apart from one another. The screwdriver 10 can therefore be rotated about a certain angle alpha relative to the male part 50 before the thickened ends 17a, 17b come in contact with the protrusions 53a, 53b. This results in a rotationally fixed connection, i.e., further rotation of the screwdriver 10 causes a corresponding rotation of the male part 50.

Figure 12:
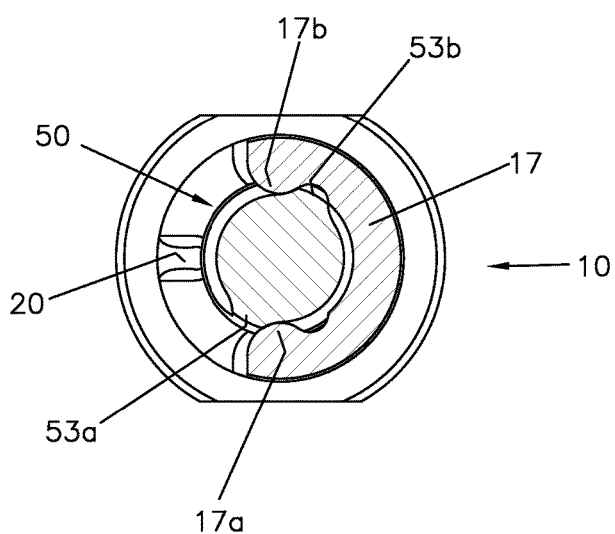
FIG. 12 shows the arrangement according to FIG. 11 in a sectional view according to line XII-XII in FIG. 11.

FIG. 12 illustrates the situation in which the screwdriver 10 has been rotated counterclockwise, so that the protrusion 53a is in contact with the end 17a on the outside and the protrusion 53b is in contact with the end 17b on the inside.

The male part 50 is optionally tightened as far as to the end position by placing a torque wrench on the handling end 10c and activating it so that the applied torque is transferred via the screwdriver 10 to the male part 50. As security against overtightening, the connecting end 10a of the screwdriver 10 can be designed so that when a threshold torque value is exceeded the ends 53a, 53b are pushed apart from one another and the protrusions 17a, 17b can slip over them and/or so that the screwdriver is bent away.

The screwdriver 10 is separated from the male part 50 by a lateral movement, so that a force is exerted on the nose 20, pushing it away and thus releasing the receiving opening 14, and the connecting end 50a can be pulled away from the head 51.

The angle alpha by which the screwdriver 10 and the male part 50 can be rotated relative to one another before there is a transfer of torque is greater than 90 degrees here and corresponds to somewhat less than half of one rotation. Such a design of the relative rotational movement facilitates in particular the mounting and the separation of the screwdriver 10 when the male part 50 is in a patient's mouth and therefore a certain positioning of a tool is made difficult because of the tight space situation.

A tightened male part 50 is released in a manner similar to that for tightening by laterally inserting the screwdriver 10 onto the male part 50, rotating the screwdriver 10 until the ends 17a, 17b and protrusions 53a, 53b contact one another and rotating further in the same direction, so that the male part 50 is released and unscrewed.

Numerous modifications of the preceding description will be available to those skilled in the art without going beyond the scope of protection of the invention as defined by the claims.

The instrument need not necessarily be used as a screwdriver. It is conceivable for it to be used in general for handling a dental part. For example, the dental part may be a male part that can be introduced into the mouth by merely shifting and pressing in the longitudinal direction. Accordingly, the instrument, which extends in the longitudinal axis between the handling end and the connecting end, may have a receiving opening, which is laterally open so that the connecting end and the dental end can be connected by displacing them relative to one another across the longitudinal axis. If handling by rotation of the dental part is not provided, then the stops 17a and 17b, among others, may be omitted.

The instrument optionally has at least one holding means, for example, one or more spring noses, for example, in the form of the nose 20, which serves to hold the head of the dental part accommodated in the receiving opening to counteract separation of the connecting end and the head. This design allows aspiration-proof handling of the dental part in particular.

The connecting end of the instrument may optionally also have a shoulder, which extends over an angular range around the longitudinal axis, this range being less than 360 degrees, preferably less than 270 degrees, and being engageable with a groove formed in the dental part.

The head of the male part may also be designed differently than that shown in FIGS. 8 through 10. For example, it may be conical, spherical or have a different shape. The receiving opening (14) of the instrument is adapted accordingly to be able to insert the head of the male part. The male part preferably has a groove (52), which can be brought into engagement with the instrument.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A male part configured to be connected to an instrument for rotation about an axis of rotation, the instrument comprising a receiving opening that is laterally open, wherein the male part comprises:
    a fastening end for releasably fastening in a mouth; and
    a head end for releasable connection to a female part that is configured to be fastened to a dental prosthesis, the head end comprising an end surface at a terminal end of the male part,
    wherein the head end comprises at least one protrusion protruding transversely to the axis of rotation, and the at least one protrusion is configured to contact a stop formed on the instrument by displacing the male part and the instrument relative to one another transversely to the axis of rotation so that the head end of the male part is received in the receiving opening of the instrument and by subsequently rotating the male part and the instrument relative to one another around the axis of rotation so that the at least one protrusion contacts the stop;
    wherein the end surface of the head end is unslotted.

2. The male part according to claim 1, wherein the head end of the male part comprises a groove extending in a plane transversely to the axis of rotation, and the groove is engageable with the instrument.

3. The male part according to claim 2, wherein the at least one protrusion is arranged at the level of the groove.

4. The male part according to claim 2, wherein the groove has a tapering cross section, and the groove tapering in a direction transversely to the axis of rotation.

5. The male part according to claim 2, wherein the male part comprises a circumferential collar arranged between the fastening end and the groove.

6. The male part according to claim 5, wherein the collar has a diameter greater than a diameter of the head end.

7. The male part according to claim 1, wherein the fastening end is a thread end that is rotatable around the axis of rotation.

8. The male part according to claim 1, wherein the at least one protrusion extends over an angular range around the axis of rotation, which is less than an angle, wherein the angle is one of 180 degrees, 90 degrees and 45 degrees.

9. The male part according to claim 1, wherein the head end comprises an end face having a contour with a convex shape.

10. The male part according to claim 1, wherein the head end comprises an end face having a contour with a planar shape.

11. The male part according to claim 1, further comprising a circumferential disc-shaped collar.

\* \* \* \* \*